United States Patent [19]

Yeung et al.

[11] Patent Number: 5,192,407
[45] Date of Patent: Mar. 9, 1993

[54] MEANS AND METHOD OF DETECTION IN CHEMICAL SEPARATION PROCEDURES

[75] Inventors: Edward S. Yeung; Lance B. Koutny; Barry L. Hogan; Chan K. Cheung; Yinfa Ma, all of Ames, Iowa

[73] Assignee: Iowa State University Research Foundation, Inc., Ames, Iowa

[21] Appl. No.: 472,315

[22] Filed: Jan. 30, 1990

[51] Int. Cl.$^5$ .................. G01N 27/26; G01N 27/447; B01D 57/02
[52] U.S. Cl. .............................. 204/182.8; 204/299 R
[58] Field of Search .............. 204/299 R, 182.8, 182.9

[56] References Cited

PUBLICATIONS

Yinfa Ma & Edward S. Yeung, "Indirect Fluorometric Detection of Anions in Thin-Layer Chromatography" Analytical Chemistry, vol. 60, No. 7 (Apr. 1, 1988) 722-724.

Yinfa Ma & Edward S. Yeung, "Indirect Fluorimetric Detection of Non-Electrolytes in Thin-Layer Chromatography" Journal of Chromatography, vol. 455 (1988) 382-389.

Barry L. Hogan and Edward S. Yeung, "Indirect Fluorometric Detection in Gel Electrophoresis" Applied Spectroscopy, vol. 43 No. 2 (1989) 349-350.

Yinfa Ma, Lance B. Koutny, & Edward S. Yeung, "Laser-Based Indirect Fluorometric Detection and Quantification in Thin-Layer Chromatography" Analytical Chemistry, vol. 81, No. 17 (1989) 1931-1933.

Primary Examiner—John Niebling
Assistant Examiner—John S. Starsiak, Jr.
Attorney, Agent, or Firm—Zarley, McKee, Thomte, Voorhees & Seas

[57] ABSTRACT

A means and method for indirect detection of constituent components of a mixture separated in a chemical separation process. Fluorescing ions are distributed across the area in which separation of the mixture will occur to provide a generally uniform background fluorescence intensity. For example, the mixture is comprised of one or more charged analytes which displace fluorescing ions where its constituent components separate to. Fluorescing ions of the same charge as the charged analyte components cause a displacement. The displacement results in the location of the separated components having a reduced fluorescence intensity to the remainder of the background. Detection of the lower fluorescence intensity areas can be visually, by photographic means and methods, or by automated laser scanning.

27 Claims, 2 Drawing Sheets

MEANS AND METHOD OF DETECTION IN CHEMICAL SEPARATION PROCEDURES

GOVERNMENT PATENT RIGHTS

This invention was made with Government support at least in part under contract #W-7405-ENG-82 awarded by the Department of Energy. The Government may have certain rights in the invention.

BACKGROUND OF THE INVENTION a. Field of the Invention

The present invention relates to detection methods, and in particular, to detection methods for chemical separation processes such as gel electrophoresis and thin layer chromatography.

b. Problems in the Art

A variety of chemical separation processes are well-known within the art. These processes are utilized to determine the identity and in some cases the amount of various constituent components of mixtures.

Many chemical separation processes have been known for years and have been refined to produce very good separation results. For example, gel electrophoresis and thin layer chromatography achieve valuable separation results for eligible mixtures and components. The separation information for these types of processes is contained in basically a two-dimensional image.

However, significant problems still remain with respect to detection and quantification of the separation results. For example, in gel electrophoresis, the ability to detect the separated components to a high degree of accuracy and reliability requires time-consuming, labor intensive methods. Even with the slow and laborious methods, detection results are also not always as good as would be desired. The present methods of detection for such separation processes are therefore costly in the sense of time, labor, and materials.

Additionally, although many of the detection processes currently utilized give fairly acceptable results, notwithstanding the above mentioned problems, most are only available for certain types of separation processes or certain types of mixtures or constituent components. Therefore, there is a real need in the art for a more universal detection system.

Another example of the need for an improved detection system is the requirement of some presently known detection processes to alter or otherwise destroy the samples of the mixture being separated to derive detection of the constituent components. It would be beneficial and desirable to have a detection method which would be nondestructive, in the sense that it would not permanently alter a mixture under analysis and allow recovery of the separated components.

It can therefore be seen that there is a real need in the art for an improved, more universal detection method for these types of chemical separation processes.

It is therefore a primary object of the present invention to provide a means and method of detection in chemical separation procedures which solves or improves over the problems and deficiencies in the art.

Another object of the present invention is to provide a means and method as above described which is much faster and less labor intensive than present procedures.

A further object of the present invention is to provide a means and method as above described which is more efficient at least with regard to labor, materials, and time.

A further object of the present invention is to provide a means and method as above described which provides better detection results while retaining the same sensitivity and reliability of separation of constituent components of a mixture.

Another object of the present invention is to provide a means and method as above described which is nondestructive to the mixture being analyzed, and does not require any alteration or addition to the mixture being analyzed.

A still further object of the present invention is to provide a means and method as above described which indirectly detects separated constituent components of the mixture and does not rely on detection of some specific property of the mixture being analyzed.

Another object of the present invention is to provide a means and method as above described which is applicable to different chemical separation processes, can be used for a wide variety of mixtures to be analyzed, and is therefore more universal than most present detection systems.

Another object of the present invention is to provide a means and method as above described which is reliable, is sensitive, and provides improved levels of detectability.

These and other objects, features, and advantages of the present invention will become more apparent with reference to the accompanying specification and claims.

SUMMARY OF THE INVENTION

The present invention includes means and methods for indirectly detecting constituent components of a mixture separated in a chemical separation process. The invention saves time, labor, and expense while providing improved detection results without effecting separation efficiencies.

Additionally, the invention is generally universal in that it can be applied to a variety of chemical separation processes and mixtures, and does not require special preparation of the mixture being analyzed.

The invention indirectly detects constituent components of the chemical separation process by first preparing a generally uniform fluorescing background in relation to the chemical separation process. For example, in such separation processes as gel electrophoresis and thin layer chromatography, a fluorescing ion (and its oppositely charged counterpart) are distributed generally uniformly through the gel slab or thin layer. The invention therefore utilizes a mixture having ionic or charged constituent components (analytes) of interest to be separated.

During the chemical separation process, the ionic constituent components, by nature of their charge, will displace like-charged fluorescing ions (or their oppositely charged counterparts) and therefore produce areas of lower fluorescence intensity.

Therefore, by observing the fluorescence intensity of the entire relevant area, the separated analyte components can be indirectly detected as dark areas, or at least lower intensity fluorescence areas, than the surrounding background.

The invention provides better detection results by utilizing this contrast in fluorescence intensity to delineate the separated components, as opposed to presently used detection procedures.

The invention is much more universal because it does not require special tags or alterations to the mixture or analyte(s) prior to separation, it is useful in mixtures having analyte components of interest which do not fluoresce, and relies on the indirect detection of components, rather than on specific properties of the analyte or components for detectability.

The invention allows the separation process to be nondestructive. The constituent components can be retrieved after separation and detection.

In a further aspect of the invention, detectability can be further improved by utilizing an energy source which excites fluorescing ions to scan the area of interest after completion of the separation process, and then monitor the fluorescence intensity as the area is scanned. Such a detection procedure can improve over visual or photographic detection procedures.

DETAILED DESCRIPTION OF THE PREFERRED EMBODIMENT

Figure 1:
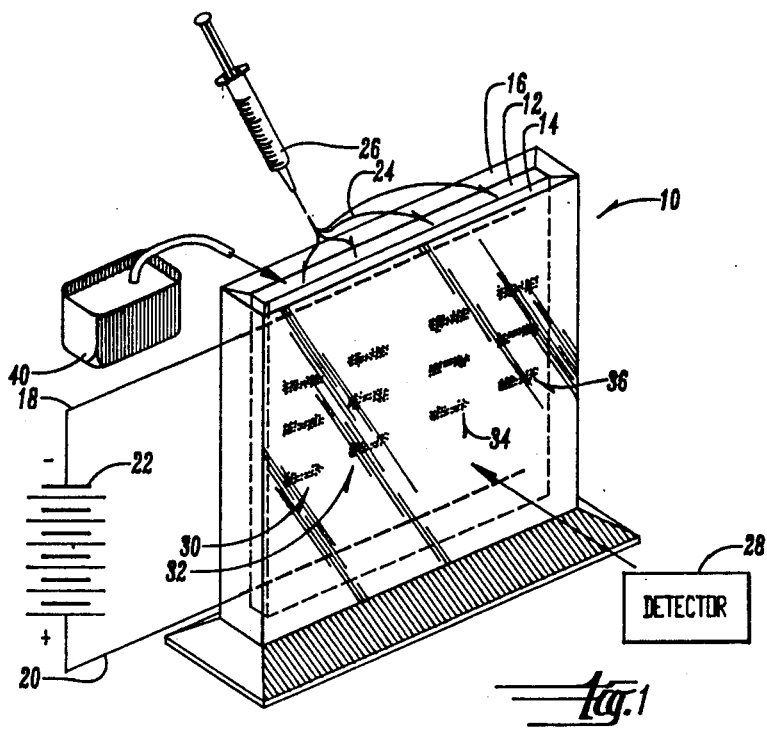
FIG. 1 is a partial perspective, partial schematic depiction of the apparatus useful in one embodiment of the present invention, namely gel electrophoresis.

A detailed description of preferred embodiments of the invention will now be described. This description is intended to aid in an understanding of the invention, but does not, nor is it intended to, specifically limit the invention in any way.

The description will be made with specific reference to the drawings. Reference numbers will be used to indicate certain elements or locations in the drawings. The same reference numbers will be used to indicate identical elements or locations throughout the drawings, unless otherwise indicated.

The present invention is to be understood to apply to both means and methods. The Summary Of The Invention has set out in general terms the means and methods of the invention. The invention indirectly detects separated charged components or analytes of a mixture in known chemical separation processes by creating a background having a generally uniform fluorescence intensity. Each analyte then displaces the fluorescing ions to present an indirectly detectable location of reduced fluorescence intensity for each particular separated analyte out of this fluorescing background.

A specific application for the invention is schematically depicted at FIG. 1. A gel electrophoresis system 10 is diagrammatically depicted. As is well-known within the art, a gel slab 12 is contained between opposite parallel glass plates 14 and 16. Electrical terminals 18 and 20 are implanted in gel slab 12 at upper and lower locations. In the preferred embodiment, terminal 18 is negative or cathodic whereas terminal 20 is positive or anodic. Electrical power source 22 provides the electrical potential between terminals 18 and 20.

A mixture 24 is injected into slab 12 at spaced apart locations along the top of slab 12 by syringe 26.

As is well-known in the art with regard to conventional gel electrophoresis, buffer solutions and other items may be added to system 10, electrical potential is provided to terminals 18 and 20, and mixture 24 is injected (generally at a plurality of points) to the slab 12. Molecular constituent components of mixture 24 will then migrate different distances within slab 12 based upon the charge and size. Basically, components that are negatively charged will migrate further towards anode 20 than ones which are positively charged. Additionally, the components with a higher negative charge will tend to migrate further towards anode 20 than those with less of a negative charge.

A detector 28 can then be positioned to view or otherwise detect what will be called vertical injection lanes 30, 32, 34, and 36 in slab 12 (containing each set of separated analytes that have rectalinearly migrated downwardly) and allow the relative distances of migration in each lane for each constituent component to be determined. As is furthermore well known in the art, previous empirical experiments utilizing similar slab material, electrical potential, and analyte components have been compiled. Therefore, the distances for the components in the embodiment of FIG. 1 can be compared to the empirical knowledge to correlate components of FIG. 1 to the known empirical information to identify each constituent component.

It can therefore be seen that it is critical that each constituent component or analyte (shown as horizontally separated bars 29a, 29b, and 29c in FIG. 5A) in lanes 30, 32, 34, and 36 be accurately detectable. The present invention accomplishes this function as follows.

In FIG. 1, a buffer solution 40 is added to electrophoresis system 10 between plates 14 and 16. Buffer solution 40 contains fluorescing ions and counter ions. Buffer solution 40 is spread uniformly through electrophoresis setup 10 so that the fluorescing ions or fluorophores, when excited, will provide a generally uniform fluorescent background across the entire gel slab 12.

In electrophoresis system 10, the uniform distribution of fluorophores is accomplished by introducing the electrical potential to slab 12 while adding the buffer solution 40 and running system 10 in this mode for a period of time. The fluorescing ions and counter ions, being of opposite polarities, will therefore tend to generally distribute themselves uniformly through slab 12.

Figures 2, 3:
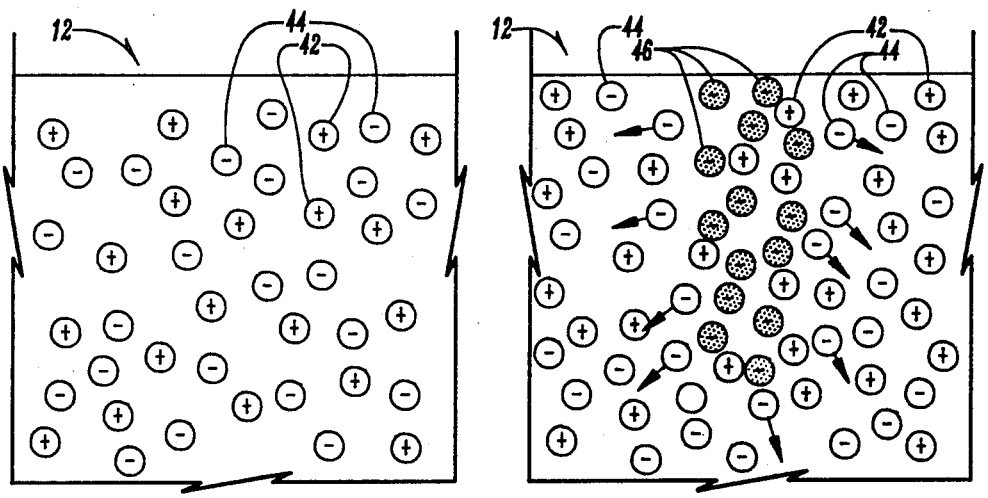
FIG. 2 is a diagrammatic view of the uniform distribution of fluorescing ions in a separation background.
FIG. 3 is a diagrammatic view of FIG. 2, but showing the displacement of fluorescing ions by a migrating ionic analyte.

FIG. 2 is a diagrammatical elevational view of a portion of gel slab 12 of FIG. 1. The fluorescing ions 42 (negatively charged) and counter ions 44 (positively charged) are depicted generally uniformly distributed through that area.

When samples of mixture 24 are then injected to the top of gel slab 12 in four separate locations, and migrate down lanes 30, 32, 34, and 36 as the electrical potential is applied to slab 12, the negative ions of each analyte (see reference numerals 46 in FIG. 3), will displace like charged fluorescing ions 42 due to local conservation of charge. As depicted in FIG. 3, this will cause the location of negative ions 46 of analyte 24 to move out the like-charged fluorophores. Thereafter, when the fluorophores are excited and fluoresce, the areas occupied by negative ions 46 of analyte 24 will have a lesser fluorescence intensity than other areas of gel slab 12.

Thus, by monitoring the fluorescence intensity across gel slab 12, the location of the separated constituent elements (negative ions 46 of each analyte 29a, b, and c) can be indirectly detected.

In FIG. 1, detector 28 can be a number of things. Detector 28 can be simply the human eye. The variation in fluorescence intensity can visually be detected, and physically the portions of the lower fluoresce intensity areas can be measured from a reference position, such as the top of slab 12. The measurements can therefore be correlated with empirical data to identify the constituent elements.

It is to be understood that detector 28 could also simply be a camera which would take a photographic image showing variations in fluorescence intensity cross slab 12. Measurements could be physically made on the photograph to identify distances and correlate to identify constituent elements.

It can therefore be seen that the present invention can advantageously be utilized with gel electrophoresis to identify ionic components of the mixture.

Two specific examples of the use of the invention with respect to gel electrophoresis are where the mixture 24 is either a mixture of ionic protein analytes or ionic DNA fragment analytes. Each will be discussed in further detail below.

EXAMPLE 1

A polyacrylamide slab gel of dimensions 8 cm ×10 cm ×0.05 cm was cast according to K. Weber and M. Osborn, as set forth in THE PROTEINS, H. Neurath & R. Hill, Eds. (Academic Press, New York, N.Y., 1975), Vol. 1, pg. 179. No buffering ions such as phosphate, or detergent such as SDS, was included with the acrylamide-water solution making up the gel. Gels were approximately 11% T and 2.7% C, where T and C and defined in S. Hjerten, Arch. Biochem. Biophys. Suppl. 1, 147 (1962). Gels were allowed 90 minutes polymerization time before use and were not stored overnight.

Cathodic electrophoresis buffer consisted of $10^{-5}$ M disodium fluorescein with $10^{-5}$ M sodium bicarbonate adjusted to a final pH of 10.5 with sodium hydroxide. Anodic buffer consisted of 26 grams of sodium hydroxide per liter of deionized water.

In this example, gel electrophoresis is utilized to separate complex mixtures of proteins. The proteins in the mixture were lyophilized soybean trypsin inhibitor (STI) and bovine serum albumin (BSA). These two proteins were dissolved in a one-to-one ratio in a 5% v/v glycerol solution. The final sample concentrations of the individual proteins were 1 $\mu g/\mu L$ or 3 $\mu g/\mu L$. Samples were prepared fresh or stored at 4° C.

The slab gel was positioned in a Bio-Rad Mini-Protean II vertical slab cell (available from Bio Rad, Richmond, Calif.). A platinum wire immersed in a buffer reservoir external to the actual cell served as the cathode. Cellulose wicks (Bio-Rad Ultra Wicks) served as the current bridge between the reservoir and the cell cathode compartment. The external reservoir partially isolated the gel from pH increases caused by cathodic electrode reactions.

The gel is pre-run for one hour at a constant power of four watts in order to achieve a uniform fluorescent background. Samples were then applied via a microsyringe. The separation by gel electrophoresis was achieved with a two-step current curve. A constant current of two milliamperes is applied for 15 minutes, followed by a constant current of ten milliamperes for 20 minutes.

Following separation an ultraviolet lamp emitting at 312 nanometers (nm) (available from Cole Parmer, Model No. J-9 815-70 UV lamp) irradiated the gel slab. The ultraviolet radiation excited the fluorescing components of the buffer in the gel proportionate to concentration of the fluorescing ions in various locations through the gel slab. The location of the separated proteins can easily be observed with the unaided eye in a darkened room, thereby comprising the indirect detection of the separated protein components of the mixture.

Figures 5A, 5B:
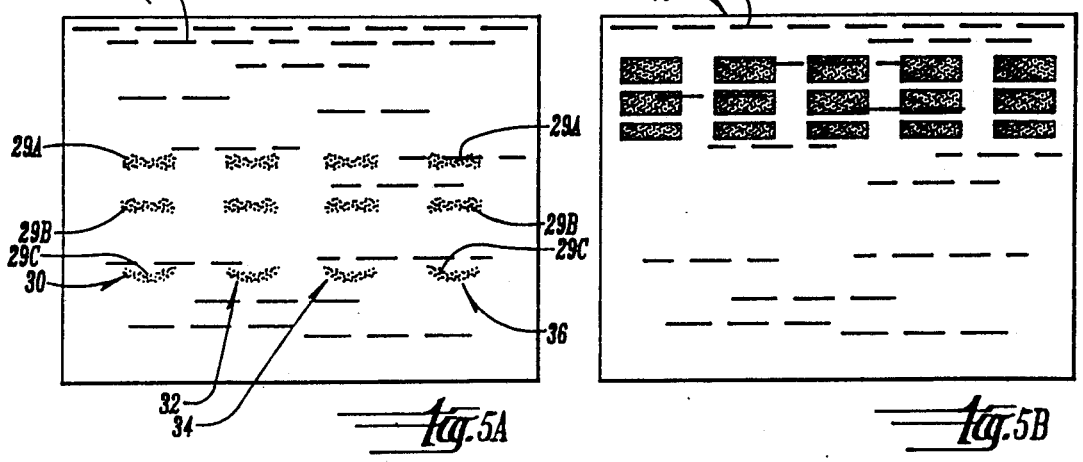
FIGS. 5A and B are diagrammatic depictions of visual records of separated protein and DNA fragment analytes, respectively, in gel electrophoresis.

By referring to FIG. 5a, a schematic depiction of a photograph of such a separation can be seen. In each lane 30, 32, 34, and 36 from left to right, the quantity of each protein is 0.5 $\mu g$, 1 $\mu g$, 3 $\mu g$, 4.5 $\mu g$. Three analytes 29a, 29b, and 29c are separated in each lane 30, 32, 34, and 36 and appear as dark bars against the fluorescing background.

EXAMPLE 2

Separation of DNA fragments in gel electrophoresis and indirect detection of the same, according to the invention, is accomplished as follows. An agarose gel slab (7 cm ×10 cm ×0.3 cm) was cast consisting of 0.8% (w/v) utilizing ultrapure DNA grade agarose which was available from the Bio-Rad Company.

The electrophoresis buffer contained 3 mM glycine 0.1 mM coumarin 343, adjusted to a final pH of 10 with sodium hydroxide.

The DNA fragments were Hind III digested fragments of Lambda DNA from Bethesda Research Laboratories and were mixed in a solution containing 10 mM Tris-HCl, 5 mM NaCl, and 0.1 mM EDTA at a concentration of 0.71 $\mu g/\mu l$. The original Bethesda Research Laboratories DNA solution was desalted and concentrated using the Millipore Ultrafree-MC Filter Unit (Catalog No. UFC3 LGC 00). The concentration of the desalted DNA sample was 1.6 $\mu g/\mu l$.

As is well known within the art, the gel was cast in an electrophoretic tray, the gelatin process of the gel was completed within 15 minutes, and sample wells were formed by an eight-tooth comb which had 5 mm ×1 mm teeth. The loading DNA solutions were prepared by diluting the desalted sample with various amounts of 8% sucrose solution. Typically, 3 $\mu l$ of the loading DNA solutions were applied to the wells that correspond to 0.9 to 2.1 $\mu g$ DNA applied.

Electrophoresis was carried out in a Bio-Rad Mini-Sub DNA Electrophoresis Cell. The electrophoretic tray with the agarose gel was submerged in the cell about 3 mm below the buffer level.

Electrophoresis was conducted at a constant voltage of 60 volts (6 V/cm) for seventy minutes. The current was approximately 5 milliamperes. To minimize band distortions caused by pH and ionic effects, buffer recirculation began 15 minutes after the starting of the electrophoretic run with the aid of a peristaltic pump.

Following separation, the gel slab was viewed under a Cole-Parmer Model 9815 Ultraviolet Lamp emitting at 254 nanometers. The indirect fluorescence signal of most of the DNA fragments could be easily observed with the unaided eye.

By referring to FIG. 5b, a schematic depiction of a photograph of the slab gel after separation is shown. The photograph displays the indirect fluorescence signal of the separated DNA fragments (depicted as sets of three separated bars in each of the vertical five lanes of the gel). The size of the fragments were (top to bottom) 23.1, 9.4, 6.6, 4.4, 2.3 and 2.0 kilobase pairs. The total amount of DNA in each lane was (left to right, 0.09, 1.2, 2.1, 0.9, and 2.1 μg.

It can therefore be seen that the invention achieves at least all of its stated objectives. As explained in the examples set forth above, detection of the analytes is accomplished indirectly in that the primary signal detected is fluorescence of the background, not any property of the mixture or its constituent analyte components. Fluorescent ions and their counter ions, distributed homogeneously throughout the gel provide a uniform level of background fluorescence in all areas of the gel prior to introduction of the specimens of the mixture. When charged analyte molecules migrate into the gel, they displace charged fluorophores (of the same sign) due to local conservation of charge.

In Example 1, a uniform distribution of anionic fluorophore and its sodium counter ion in the gel is produced. As a fixed number of sodium counter ions exist in any given location of the gel, migration of anionic protein molecules into the gel must cause displacement of an equivalent amount of the anionic fluorophore from that region in order that local charge balance be maintained. Upon displacement, the region of the gel containing the analyte is then seen to have a decreased level of fluorescence relative to the gel background, due to the reduced number of fluorophores present in that region. Therefore, detection is based upon charge displacement, not upon the absorption or emission properties of the analyte.

As has been discussed, the indirect detection according to the invention allows detection to be made in a variety of ways including with the unaided eye or with still photography. The process of deriving the identity of the analyte components can then be easily accomplished utilizing known procedures, as is well known to those of ordinary skill in the art and as has previously been discussed. It should therefore be understood that alternatively, an automated detector can be utilized to improved detectability.

Figure 4:
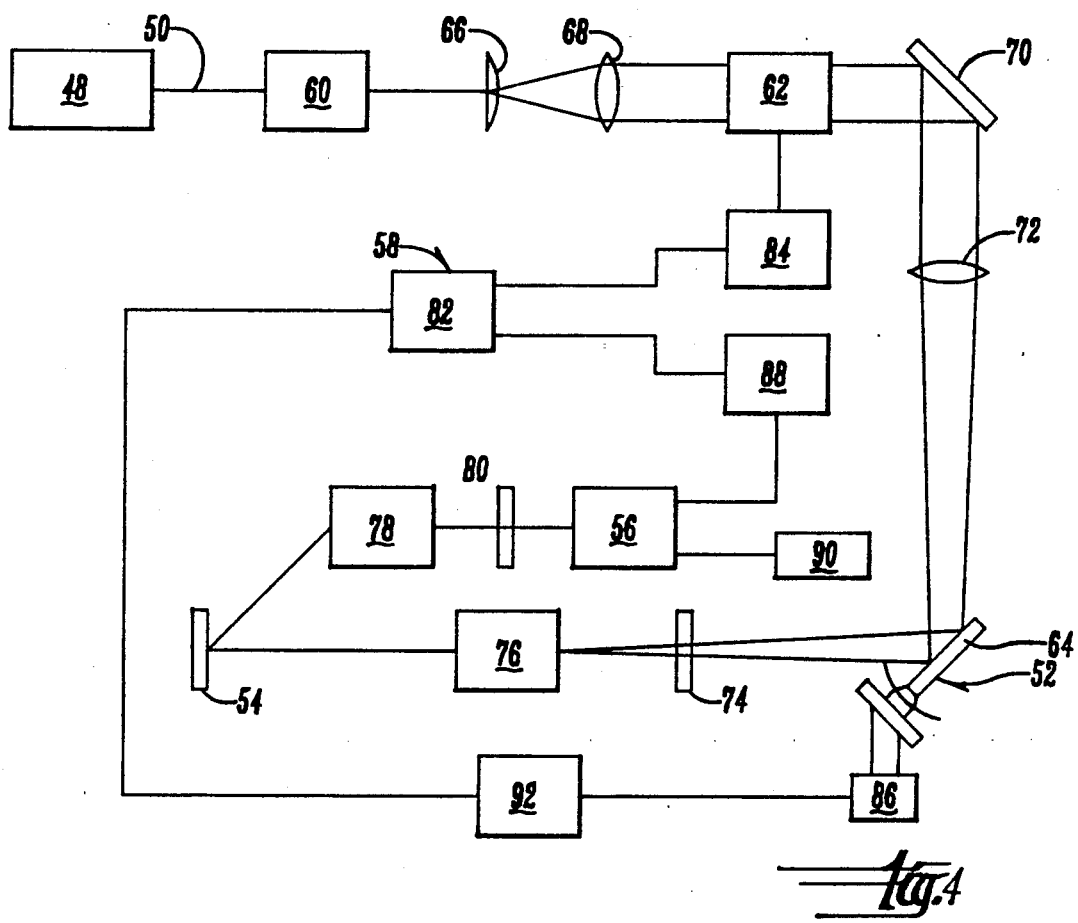
FIG. 4 is a schematic view of an alternative embodiment of the present invention applied to thin layer chromatography and utilizing a laser scanning detection system.

One embodiment for such automated detection is shown in FIG. 4. A laser scanner system with automated data collection and signal averaging is utilized. It is to be understood that the use of laser excitation can allow the concentration of the fluorescent buffer ion to be reduced substantially which would decrease the limiting detectable concentration proportionally. It could also make possible such options as separations of analytes within quartz capillary tubes (for example 75 micrometers internal diameter), which in turn would reduce the cross-sectional area of the gel involved in the separation and improve mass detectability proportionally. Miniature separations of this type have applications in areas such as the analysis of single cells for neurological studies. It is to be understood that the invention also could be utilized in gene sequencing and mapping and clinical diagnoses.

FIG. 4 depicts the utilization of a laser scanner system in association with thin layer chromatography, which is analogous to gel electrophoresis in that separation of constituent analyte components of the mixture is accomplished by migration through a two-dimensional medium. As with the previously described examples of gel electrophoresis, the mixture in thin plate layer chromatography may be ionic, and each separated analyte portion would displace like-charged fluorophore at its location across a surface matrix associated with a thin plate. While indirect detection, even with the unaided eye, could again be accomplished, the automatic detection system shown in FIG. 4 utilizes a laser source 48 which produces a laser beam 50. Beam 50 is directed through a variety of components to a scanning mirror 52 which in a controlled manner directs beam 50 in a raster scan (x-y two-dimensional scan) of the surface matrix of plate 54 of the thin layer chromatography system. A detector in the form of a photomultiplier tube (PMT) 56 can perceive variations in fluorescence intensity as the laser scans across plate 54, converts those variations into a signal which is then communicated to a control unit 58 (generally a computer) which can store such data and compile it in a fashion that it can be correlated and used to calculate the identity of the indirectly detected separated constituent components in the thin layer chromatography.

As with gel electrophoresis, the detector with respect to FIG. 4 responds to a physical property of something other than of the analyte itself. When the analytes elute, displacement of the eluent causes a change in the background signal. An ultraviolet lamp can be used to perceive by indirect detection the separated analytes, but with the laser scanning system, a high sensitivity and wide linear dynamic range can be achieved. The thin layer chromatography plate 54 and detector PMT 56 are fixed, while the laser beam 50 is scanned. The control unit 58 controls the X-Y raster scanning and concurrently collects data.

A specific example is described below.

EXAMPLE 3

In the thin layer chromatography system of FIG. 4, automatic detection was accomplished. A total data acquisition time of 35 seconds for a data array of 256×64 was achieved. Data was also averaged to improve the signal-to-noise ratio (S/N).

Laser source 48 was a He-Ne laser available from Uniphase, Manteca, Calif. Laser source 48 used an excitation light source at 633 nm at a power of 8 mW.

A laser power stabilizer 60 available from Cambridge Research and Instrumentation, Cambridge, Mass. under product number LS100, was used to maintain a constant laser power. A radio frequency (rf) driver 84 controlled an acoustooptic modulator 62 available from Andersen Laboratories, Inc., Bloomfield, Conn. which was used to deflect laser beam 50. A change in the frequency of rf input to modulator 62 causes deflection of the first-order laser beam such as is described at Lekavich, J. Lasers Appl. 1985, 4, 59–64, and in Young, M. Optics and Lasers, Springer-Verlag; Berlin 1986; p. 193.

Modulator 62 and a rotating mirror 64 combine to scan beam 50 in horizontal and vertical directions respectively. To obtain optimum spatial resolution, a cylindrical beam expander utilizing lenses 66 and 68 was used along with mirror 70, and long focal length lenses 72 and 74, where indicated in FIG. 4. The focused image onto a microscope eyepiece 76 (12× magnification) was enlarged to an area of 40×50 mm (horizontal × vertical) with a laser spot size of about 1.5 mm on the thin layer chromatographic plate 54.

The detector included a camera lens 78 (available from Vivitar Corporation, Santa Monica, Calif., 28–105 mm, f2.8–f3.8) which collected the fluorescence signal, passed it through a cut-of filter 80 (to remove scattered 633-nm light) and directed it into PMT 56 operated at 850 V (available from Hamamatsu, Middlesex, N.J. under product No. R928).

The output of PMT 56 was converted into voltage via a resistor (not shown) and fed into a data acquisition system consisting of an analog to digital I/O interface available from Data Translation, Marlborough, Mass. under product designation DT 2827, and a microcomputer, in this instance an IBM PC/AT available from IBM, Boca Raton, Fla. The microcomputer 82 controlled the rf output device 84 which in turn controlled modulator 62, as well as controlling a stepper motor 86 which controlled rotating mirror 64, which provided the x-y scan for beam 50. Control of modulator 62 and mirror 64 was synchronous.

The rf output device 84 is a radio frequency driver; while I/V component 88 is a current-voltage converter. HV device 90 is a high voltage power source whereas device 90 represents power for stepping motor 86.

In this embodiment, lens 66 is a 25 mm focal length cylindrical lens; lens 68 is a 400 mm focal length spherical lens; lens 72 is 1000 mm focal length spherical lens; and lens 74 is a 250 mm focal length cylindrical lens.

The thin layer chromatography utilized a $K_6$ silica gel plate available from Whatman of Clifton, N.J. The plate was pretreated with $2 \times 10^{-6}$ M Nile Blue A perchlorate in methanol for 20 minutes. The plate was then dried with a heat gun. A 0.1–1.0 μL methanol solution of test sample containing crocein orange G and orange G available from Aldrich of Milwaukee, Wis. was spotted with a microsyringe available from Hamilton of Reno, Nev.

The thin layer plate was developed to a distance of about 40 mm from the origin in a developing solution containing 2-butanol/acetone/water (75:15:10) (v/v)). After drying, the thin layer chromatography plate was placed in the apparatus for measurements, as depicted in FIG. 4.

It is to be understood that Nile Blue was used as the fluorophore because it can be excited by a He-Ne (helium-neon) laser. Other fluorophores can be utilized.

Analytes were chosen so that they do not absorb at the He-Ne laser wavelength or fluorescence wavelength.

It is to be understood that the laser scanner could therefore be used to advantageously detect indirectly the separated components in Example 3. It could likewise be used for processes such as set forth in Examples 1 and 2.

It will be appreciated that the present invention can take many forms and embodiments. The true essence and spirit of this invention are defined in the appended claims, and it is not intended that the embodiment of the invention presented herein should limit the scope thereof.

What is claimed is:

1. The method of detection of certain components of a mixture in gel electrophoresis, comprising:
    taking an encapsulated gel segment comprised of a gel slab means;
    impregnating said gel segment with a fluorescing substance comprised of positive and negative ions to create a generally uniform background fluorescence across said segment when the fluorescing substance is excited;
    imposing an electrical potential through said segment to enable electrophoresis;
    injecting in said gel segment a liquid specimen of an ionic mixture having constituent ionic molecular components to be detected, each component having an ionic charge of one of the set consisting of positive and negative charges, whereby each component of said specimen will generally rectalinearly migrate in said gel segment according to type and magnitude of electrical charge and will create a negative image at the end of migration by displacing the identically charged ions of the fluorescing substance in that general area within said gel segment;
    measuring the length of the rectalinear migration of each negative image within said gel segment; and
    comparing said length of migration of any negative image within said gel segment with lengths of migration of known ionic molecular components in a similar gel segment to identify the components of the mixture by correlating said lengths of migration with known ionic molecular components having similar lengths of migration.

2. The method of claim 1 wherein said mixture is a mixture including ionic protein components.

3. The method of claim 1 wherein said mixture is a mixture including ionic DNA components.

4. The method of claim 1 wherein the step of measuring includes visually identifying any negative image and physically measuring the length of migration of said image within said gel segment.

5. The method of claim 1 wherein the step of measuring includes making a visually perceivable record of any negative image within the fluorescing gel segment and physically measuring the length of migration of said image on the visually perceivable record.

6. The method of claim 1 wherein the step of measuring includes scanning a laser means across the gel segment, recording the fluorescence intensity with a light sensitive means, producing a signal representative of fluorescence intensity during scanning, and utilizing the signal to resolve the length of migration of any negative image by comparison of differences in fluorescence intensity represented in the signal.

7. The method of claim 6 further comprising converting the signal into a voltage signal, the voltage signal being adaptable for use by a computing means.

8. The method of claim 1 wherein the gel slab means comprises polyacrylamide gel.

9. The method of claim 1 wherein the fluorescing substance comprises a mixture of fluorescent ions and counter ions.

10. The method of claim 9 wherein the fluorescent ions are comprised of disodium fluorescein mixed with sodium bicarbonate adjusted to a pH of 10.5 with sodium hydroxide to produce a fluorescing cathodic electrophoresis buffer.

11. The method of claim 10 wherein the counter ions are comprised of a combination of sodium hydroxide and deionized water.

12. The method of claim 1 wherein a uniform fluorescent background is created by imposing the electrical potential for a time period before injecting the liquid specimen in the gel segment.

13. The method of claim 1 wherein a plurality of specimens are injected in said gel segment.

14. The method of claim 1 wherein the step of measuring is conducting while imposing ultraviolet light onto the gel segment in a darkened room.

15. The method of claim 1 wherein the gel segment is substantially encapsulated between two plate means.

16. The method of claim 1 wherein the gel segment is encapsulated in a capillary tube.

17. The method of claim 2 wherein the ionic protein components are lyophilized soybean trypsin inhibitor and bovine serum albumin dissolved in glycerol solution.

18. The method of claim 1 wherein multiple ionic molecular components create multiple negative images along the rectilinear migration for each injected specimen.

19. The method of claim 1 wherein each negative image includes a negative image band.

20. The method of claim 1 wherein the fluorescing substance is a fluorophore.

21. The method of claim 1 wherein the mixture is an analyte.

22. The method of claim 19 wherein the fluorophore is an eluent.

23. The method of claim 1 wherein the ionic molecular components of the mixture do not contain fluorescent tags.

24. The method of claim 1 wherein the mixture, including ionic molecular components, does not fluoresce.

25. A method of detection of certain components of an ionic mixture separated or gel electrophoresis comprising:
   impregnating a two-dimensional medium for separating components of the mixture with a fluorescing substance comprised of positive and negative ions to create a generally uniform background fluorescence across the length and width of the medium when the fluorescing substance is excited;
   injecting in the medium one or more liquid specimens of the ionic mixture, each ionic component having a charge of one of the set consisting of positive and negative charges, whereby each constituent ionic molecular component of said specimen will generally rectalinear migrate and separate in a migration lane according to differential electrophoretic migration and will create a negative image at the end of migration by displacing the identically charged ions of the fluorescing substance in that general area within said medium;
   measuring the length of rectalinear migration of each negative image within the medium; and
   comparing said length of migration of any negative image within the medium with lengths of migration of known ionic molecular components in a similar medium to identify the components of the mixture by correlating said lengths of migration with known ionic molecular components having similar lengths of migration.

26. The method of claim 25 comprising the further step of utilizing a laser scanning system to excite the fluorescing substance as a laser is scanned to cross the length and width of the medium, and a light sensitive means for recording the fluorescence intensity caused by the laser scanning.

27. The method of claim 26 wherein the light sensitive means produces a signal representative of fluorescence intensity during scanning and comprising the further step of utilizing the signal to resolve the length of migration of any negative image by comparison of differences and fluorescence intensity represented in the signal, the lengths of migration being identified and correlated to the actual lengths of migration.

* * * * *